United States Patent [19]
Farrell et al.

[11] Patent Number: 6,060,616
[45] Date of Patent: May 9, 2000

[54] BIS-PLATINUM COMPLEXES WITH POLYMETHYLENE DERIVATIVES AS LIGANDS HAVING ANTITUMOR ACTIVITY

[75] Inventors: Nicholas P. Farrell, Richmond, Va.; Erneston Menta, Cernusco Sul Naviglio, Italy; Roberto Di Domenico, Milan, Italy; Silvano Spinelli, Monza, Italy

[73] Assignees: Hoffmann-La Roche Inc., Nutley, N.J.; Virginia Commonwealth University, Richmond, Va.

[21] Appl. No.: 09/051,468

[22] PCT Filed: Jul. 22, 1997

[86] PCT No.: PCT/US97/12552

§ 371 Date: Oct. 14, 1998

§ 102(e) Date: Oct. 14, 1998

[87] PCT Pub. No.: WO98/03518

PCT Pub. Date: Jan. 29, 1998

Related U.S. Application Data

[60] Provisional application No. 60/022,269, Jul. 22, 1996.

[51] Int. Cl.$^7$ .................................................. C07F 15/00
[52] U.S. Cl. ................................................................ 556/137
[58] Field of Search ..................................... 556/136, 137

[56] References Cited

U.S. PATENT DOCUMENTS

| | | | |
|---|---|---|---|
| 4,797,393 | 1/1989 | Farrell | 514/188 |
| 4,871,729 | 10/1989 | Farrell | 514/188 |
| 5,107,007 | 4/1992 | Farrell | 556/137 |
| 5,145,848 | 9/1992 | Pasini | 514/185 |
| 5,744,497 | 4/1998 | Valsecchi | 514/492 |
| 5,770,591 | 6/1998 | Farrell | 514/187 |

*Primary Examiner*—Gary Geist
*Assistant Examiner*—Jean F Vollano
*Attorney, Agent, or Firm*—Arent Fox Kintner Plotkin & Kahn

[57] ABSTRACT

Bis-platinum(II) complexes with polymethylene derivatives, the method of making the complexes, and the use of the complexes for the treatment of tumors in mammals, are disclosed. The method of making the polymethylene derivatives, is also disclosed.

15 Claims, No Drawings

BIS-PLATINUM COMPLEXES WITH POLYMETHYLENE DERIVATIVES AS LIGANDS HAVING ANTITUMOR ACTIVITY

This application claims benefit of Provisional Appl. 60/022,269 filed Jul. 22, 1996.

BACKGROUND OF THE INVENTION

The present invention relates to new bis-platinum complexes in which two platinum cores are connected by a polymethylene derivative ligand and to pharmaceutical compositions containing them.

The use of platinum complexes in cancer chemotherapy is well known. Cisplatin (CDDP) for example is used in therapy to treat testicular, ovarian, head and neck and small cell lung carcinomas. However, treatment with cisplatin may result in severe nephrotoxicity. A further clinical disadvantage is the problem of aquired drug resistance resulting in the tumor becoming refractory to treatment by the agent.

To overcome the nephrotoxic effects of cisplatin, a second-generation analogue, carboplatin, was developed. Carboplatin, or [Pt(NH3)2(CBDCA)] (where CBDCA stands for 1,1-cyclobutanedicarboxylate), is clinically effective against the same spectrum of carcinomas as cisplatin, but exhibits a reduction in the nephrotoxic effects.

A number of different mono- and bis-platinum complexes have been prepared in an attempt to treat different tumors or carcinomas (U.S. Pat. Nos. 4,225,529; 4,250,189; 4,553,502; 4,565,884). None of such compounds is currently used in therapy.

More recently, new bis-platinum(II) complexes are disclosed (U.S. Pat. No. 4,797,393), which have a bridging diamine or polyamine ligand and primary or secondary amines or pyridine type nitrogen-carrying ligands attached to the platinum complex, as well as two different or identical monoanionic ligands which may be a halide, phosphate, nitrate, carboxylate, substituted carboxylate or one dianionic ligand such as sulfate or dicarboxylate. The expert technician will appreciate that the complex is neutral, since two anions counter-balance the +2 charge on each platinum core.

WO 91/03482 further discloses bis-platinum(II) complexes such as those described in U.S. Pat. No. 4,797,393, the main difference consisting in having two nitrogen-carrying neutral ligands and only one simple charged ligand on each platinum core. This results in a complex having a +2 total charge. These complexes interfere with DNA replication forming interstrand cross-links, which cause conformational changes on the DNA and eventually lead to the inhibition of replication and to the final cytotoxic effect.

Even if such compounds are able to partially overcome the resistance to cisplatin in cisplatin-resistant cell lines and thus may have a broader spectrum of activity than cisplatin, nevertheless their activity against the non-resistant lines appears lower when compared with cisplatin (see Table I).

On the other hand, polyamines are considered essential in cell proliferation. The naturally occurring polyamines in mammalian cells are putrescine, spermidine and spermine. A wide variety of related amines are found in other organisms and may play critical roles in their physiology. Nevertheless, it is also known that the association of cationic polyamines with negatively charged DNA induces significant structural changes in DNA. Spermidine and spermine can cause DNA to condense and aggregate and induce B-to-Z transition in certain DNA sequences (Marton, L. J. et al., Annu. Rev. Pharmacol. Toxicol., 1995, 35: 55–91). This led the researchers to focus their attention on the potential use of polyamines as antitumor drugs (Basu, H. S. et al., Biochem. J., 1990, 269: 329–334; Yanlong Li et al., J. Med. Chem., 1996, 39: 339–341).

We have now found that modifying the polyamine chain by replacing the secondary nitrogens with different basic and not basic groups brings to bis-platinum complexes with a particularly interesting activity as antitumor agents.

Bis-platinum complexes bridged by ligands that carry two amide functionalities were disclosed in Inorg. Chem., 34, 2316-22 (1994), but in those compounds two amine groups chelate each platinum atom, which results in a different conformational behaviour with respect to the complexes of the present invention. Moreover, they bring two leaving ligands (chloride or dimethylsulphoxide) on each platinum core, therefore the total charge and the reactivity too are expected to be different.

SUMMARY OF THE INVENTION

It is an object of the present invention to provide bis-platinum(II) complexes of formula (I):

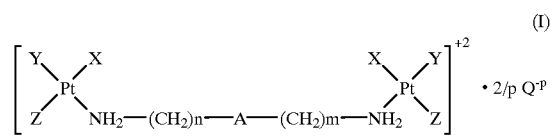

wherein:
X, Y and Z ligands are selected in the group consisting of ammonia, chloride, bromide, iodide or carboxylate of formula R—COO—$C_1$-$C_4$, in which R is a ($C_1$-$C_4$)alkyl group, with the proviso that two of X, Y and Z are ammonia, the other being selected among chloride, bromide, iodide and carboxylate R—COO—;

n and m, which can be the same or different, are an integer from 2 to 8;

p is the integer 1 or 2;

the bifunctional ligand of formula $H_2N$—$(CH_2)_n$—A—$(CH_2)_m$—$NH_2$ is a polymethylene derivative;

Q-p is a suitable counterion, comprising enantiomers and diastereoisomers thereof.

It is a further object of the present invention to provide a process for preparing compounds of formula (I).

It is another object of the present invention to provide a method of treating tumors, which are susceptible of platinum-complexes treatment, with one or more compounds of formula (I), as well as pharmaceutical compositions containing compounds of formula (I) with pharmaceutically acceptable eccipients.

DETAILED DESCRIPTION OF THE INVENTION

It is an object of the present invention to provide bis-platinum(II) complexes of formula (I):

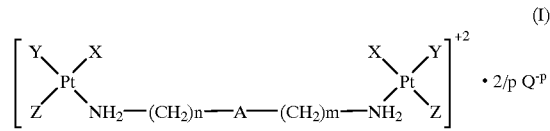

wherein:
X, Y and Z ligands are selected in the group consisting of ammonia, chloride, bromide, iodide or carboxylate of formula R—COO—, in which R is a $(C_1-C_4)$alkyl group, with the proviso that two of X, Y and Z are ammonia, the other being selected among chloride, bromide, iodide and carboxylate R—COO—;

n and m, which can be the same or different, are an integer from 2 to 8;

p is the integer 1 or 2;

A is selected in the group consisting of —$B_1$— and —$B_2$—$(CH_2)_r$—$B_2$—, wherein r is an integer ranging from 2 to 8, $B_1$ is selected in the group consisting of —$NR^1$—CO—, —CO—$NR^1$—, —$NR^1$—$SO_2$—$NR^1$—, —$NR^1$—C(=$NR^2$)—$NR^1$—, —$NR^1$—CO—CO—$NR^1$— or —$NR^1$—CO—$NR^1$—, and $B_2$ is a —$NR^1$—CO— or —CO—$NR^1$— group, in which $R^1$ is hydrogen or a $(C_1-C_4)$ alkyl group and $R^2$ has the meanings of $R_1$ or is a tert-butyloxycarbonyl group;

$Q^{-p}$ is an anion selected from chloride, bromide, iodide, nitrate, sulfate, hydrogensulfate, perchlorate.

Enantiomers and diastereoisomers of the compounds of formula (I) are also encompassed in the scope of the present invention.

Preferred compounds of formula (I) are those in which A is a $B_1$ group and $B_1$ has the above meanings.

Particularly preferred compounds of formula (I) are those in which $B_1$ is a —NHCO—, —CONH—, —NHCONH— or —NHCO—CONH group.

More particularly preferred compounds of formula (I) are those in which, further to the above limitations, the two platinum cores have the ligands in trans configuration.

"Trans configuration" means in the compounds of formula (I) that the two ammonia groups are in trans position, i.e. X and Z are ammonia, the other being as above defined.

The complexes of formula (I) may be prepared according to a procedure which encompasses the following steps:

(a) reaction of a precursor of formula [Pt(X)(Y)(Z)Cl], wherein X, Y and Z are as above defined and wherein the two ammonia groups may be in cis or trans configuration, in dimethylformamide in the presence of equimolar amount of $AgNO_3$, to give the activated intermediate of formula (II):

[Pt(X)(Y)(Z)(DMF)]⁺$NO_3^-$ (II)

(b) condensation of two moles of intermediate (II) with a polymethylene derivative of formula (III):

$H_2N$—$(CH_2)_n$—A'—$(CH_2)_m$—$NH_2$ (III)

in which A' has the meanings of A or is a group that can be converted into A by removal of suitable protecting groups, obtaining a Pt complex of formula (I'):

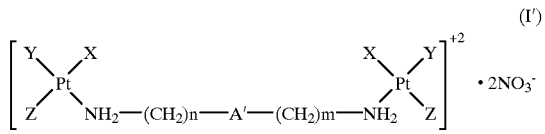

wherein all the variables are as above defined;

(c) removal of the protecting groups optionally present;

(d) separation of diastereoisomers optionally formed by conventional chromatographic methods.

The precursors of formula [Pt(X)(Y)(Z)Cl] are known compounds and some of them are commercially available.

The nitrate counterion in the outer coordination sphere can optionally be exchanged with other anions to give other compounds of formula (I).

Step (a) can be performed at temperatures ranging from 0° C. and 50° C., preferentially at room temperature.

Step (b) can be performed at temperatures ranging from −40° C. to room temperature, preferentially −20° C. A 10% to 100% molar excess of platinum intermediates of formula (II) may be used.

Suitable protecting groups which can be used in the present invention are all the protecting groups generally used for molecules containing basic nitrogen atoms. A particularly suitable protecting group is the tert-butyloxycarbonyl group. As stated above, compounds in which $R^2$ is a tert-butyloxycarbonyl (BOC) group are also encompassed in the scope of the present invention. They can further be converted into other compounds of formula (I) in which $R^2$ is hydrogen by removal of the BOC group according to step (c).

Step (c) is performed according to conventional methods for the removal of a secondary amine's protecting group. For example, when the tert-butyloxycarbonyl protecting group is used, its removal can be performed by treatment with an organic or inorganic acid, such as treatment with hydrochloric acid in aqueous or in water/methanol solution.

The intermediates of formula (IIIa), in which $B_1$ is a —$NR^1$—CO— or —CO—$NR^1$— group, can be prepared according to the scheme I. The intermediates of formula (IIIb), in which A' is a —$B_2$—$(CH_2)_r$—$B_2$— group and $B_2$ is a —$NR^1$—CO— or —CO—$NR^1$— group, can be prepared according to the scheme II.

The process shown in schemes I–II comprises the steps of:

(e) protection of the nitrogen atom of an w-aminoacid with a suitable protecting group, preferentially a tertbutyloxycarbonyl group, followed by the treatment with a mineral acid, to obtain the not salified acid;

(f) mono-protection of a diamine with a suitable protecting group, preferentially tert-butyloxycarbonyl group;

(g) reaction of the intermediate obtained in step (e) with that obtained in step (f) to give the intermediate (IV) (scheme I); or alternatively, reaction of the intermediate obtained in step (e) with a diamine to give intermediate (V) (scheme II);

(h) removal of the protecting groups present in intermediates (IV) or (V), respectively.

It is evident that using analogous schemes of synthesis, via successive steps of group protection, condensation and deprotection, wherein a dicarboxylic acid is reacted with two diamines or an aminoacid is reacted successively with other two aminoacids, which can be different or equal, all the possible combinations are obtained:

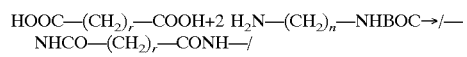

HOOC—$(CH_2)_r$—COOH+2 $H_2N$—$(CH_2)_n$—NHBOC→/—NHCO—$(CH_2)_r$—CONH—/

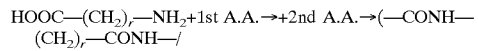

HOOC—$(CH_2)_r$—$NH_2$+1st A.A.→+2nd A.A.→(—CONH—$(CH_2)_r$—CONH—/

Step (f) can be performed using amounts of protecting reagent ranging from 0.3 to 0.5 moles per mole of diamine. Suitable protecting groups are the protecting groups for a primary amine of an aminoacid, as can be evident to the expert technician, such as those reported in Green, T. W., Wuts, P. G. M., "Protective Groups in Organic Synthesis", Second Edition, John Wiley & Sons, 1991.

The condensation reaction of step (g) can be performed by activating the carboxylic functionality with methods known to the expert of the art, such as treating it with SOC12 to give the acyl chloride, or treating the same with N,N'-carbonyidiimidazole; alternatively, the two intermediates can be condensed using a suitable condensing agent, such as dicyclohexylcarbodiimide and the like.

The removal of the protecting groups in step (h) is related to the protecting group which has been used. In particular, when tertbutyloxycarbonyl group is used, then its removal may be performed by treatment with an acid, preferentially trifluoroacetic acid in organic solution.

It is evident that, when in step (g) of scheme II two different aminoacids are used (i.e. in which n is not the same) instead of two moles of the same aminoacid, then polymethylene derivatives of formula (IIIb), wherein n and m are different, are obtained. The reaction may be performed in two steps, optionally using a mono-protected diamine in the first step, followed by the selective deprotection of the same and by the condensation of the second aminoacid.

The polymethylene derivatives of formula (IIIc):

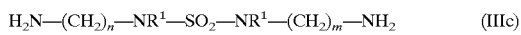

$$H_2N-(CH_2)_n-NR^1-SO_2-NR^1-(CH_2)_m-NH_2 \qquad (IIIc)$$

wherein R1 has the above meanings, can be prepared according to the following steps:

(i) condensation of two moles of monoprotected diamine with sulphuryl chloride, according to the method described in J. Org. Chem., 55, 2682–8 (1990). The reaction may be conducted in one or in two steps. In the latter case, compounds in which n and m are different can be obtained.

(I) removal of the protecting groups on the nitrogen.

Suitable protecting groups of the diamine are the protecting groups for a primary or secondary amine, as can be evident to the expert technician, such as those reported in Green, T. W., Wuts, P. G. M., "Protective Groups in Organic Synthesis", Second Edition, John Wiley & Sons, 1991. A preferred protecting group is the tert-butyloxycarbonyl group.

Step (i) is preferentially performed in an inert apolar solvent such as petroleum ether and at a temperature ranging from −10° C. to 50° C.

The removal of the protecting groups in step (I) is related to the protecting group which has been used. In particular, when tertbutyloxycarbonyl group is used, then its removal may be performed by treatment with an acid, preferentially trifluoroacetic acid in organic solution.

Polymethylene derivatives of formula (IIId):

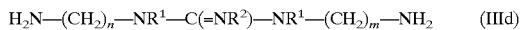

$$H_2N-(CH_2)_n-NR^1-C(=NR^2)-NR^1-(CH_2)_m-NH_2 \qquad (IIId)$$

wherein $R^1$ has the above meanings and $R^2$ is hydrogen or a tert-butyloxycarbonyl group, may be prepared according to the methods described in Tetrahedron Letters, 40, 5933–6 (1992), Organic Synthesis, Coll. Vol. IV, 180 and Synthesis, 1980, 460–6, as depicted in scheme III.

The process shown in scheme III comprises the following steps:

(m) reaction of a mono protected diamine with benzoyl isothiocyanate in an inert solvent such as chloroform;

(n) removal of the benzoyl group on the nitrogen in basic conditions (such as using a carbonate of an alkaline or alkaline-earth metal in water or in a mixture of water and an alcohol), followed by protection of the same nitrogen with a suitable protecting group;

(o) reaction of the intermediate obtained in step (n) with one mole of the same as or a different mono protected diamine than that used in step (m), in the presence of a suitable condensing agent;

(p) removal of the protecting groups which are present on the nitrogen atoms, to give compounds (IIId) in which $R^2$ is hydrogen;

(q) protection of the primary amines with a suitable protecting group, preferentially trifluoroacetyl group;

(r) protection of the guanidino nitrogen with a tert-butyloxycarbonyl group; and (s) removal of the primary amine's protecting groups to give compounds (IIId) in which $R^2$ is a tert-butyloxycarbonyl group.

Suitable protecting groups according to step (n) are the protecting groups for a primary amine, such as those reported in Green, T. W., Wuts, P. G. M., "Protective Groups in Organic Synthesis", Second Edition, John Wiley & Sons, 1991. A preferred protecting group is the tert-butyloxycarbonyl group. Suitable condensing agents according to step (o) are, for example, carbodiimides, preferentially water soluble carbodiimides such as N-(3-dimethylaminopropyl)-N'-ethyl carbodiimide.

In step (p), when a tert-butyloxycarbonyl group is used as protecting group, then its removal may be performed in acidic conditions such as by using trifluoroacetic acid in excess in an inert solvent.

An alternative method for obtaining compounds (IIId) in which $R^2$ is a tert-butyloxycarbonyl group is that described in scheme (IV).

It encompasses the steps of:

(t) protecting one nitrogen of a diamine with a suitable protecting group stable in acidic conditions, preferentially with a trifluoroacetyl group;

(u) reacting the compound obtained in step (t) with ammonium thiocyanate in acidic conditions (i.e. hydrochloric acid);

(v) protecting the primary nitrogen atom of the thiourea with a suitable protecting group, preferentially with a tert-butyloxycarbonyl group;

(z) reacting the compound obtained in step (v) with one mole of the same as or a different mono-protected diamine than that obtained in step (t); and (s) as previously described.

The polymethylene derivatives of formula (IIId) in which $R^2$ is a $(C_1-C_4)$alkyl group may be obtained according to a process which encompasses the following steps:

(1) reacting a mono-protected diamine with a N-alkyl isothiocyanate, according to the method shown in step (m);

(2) alkylating the sulfur atom with a suitable alkylating agent, preferentially methyl iodide;

(3) reacting the intermediate obtained in step (2) with the same as or a different mono-protected diamine than that used in step (1);

(4) removing the protecting groups present on the primary amines. The platinum complexes of formula (I) in which $R^2$ is hydrogen are preferentially obtained starting from intermediates (IIId) in which $R^2$ is a tert-butyloxycarbonyl group, by removing the BOC group from the guanidine nitrogen in the platinum complex already formed.

The polymethylene derivatives of formula (IIIe):

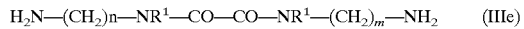

$$H_2N-(CH_2)n-NR^1-CO-CO-NR^1-(CH_2)_m-NH_2 \qquad (IIIe)$$

in which $R^1$ has the above meanings, may be obtained by a process which encompasses the steps of:

(5) reacting two moles of a mono-protected diamine as previously described with one mole of oxalyl chloride. The reaction may be performed in a single step or in two separate steps. In the latter case, by using two different mono-protected diamines, compounds (IIIe) with n and m different are obtained;

(6) removing the protecting groups present on the primary nitrogen atoms. Analogously, the polymethylene derivatives of formula (IIIf):

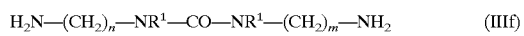

$$H_2N-(CH_2)_n-NR^1-CO-NR^1-(CH_2)_m-NH_2 \qquad (IIIf)$$

in which R1 has the above meanings, may be obtained by replacing in step (5) the oxalyl chloride with a suitable carbonyl source, such as phosgene, a dialkyl carbonate or N,N'-carbonyl diimidazole. This latter is preferentially used.

The compounds of the invention were tested for their cytotoxic effect "in vitro" on various tumor cell lines, among which murine leukemia L1210 and human ovarian carcinoma A2780 or the respective cisplatin resistant sublines L1210/CDDP and A2780/CDDP. Table (I) shows the pharmacological data for some representative compounds of the invention in comparison with cisplatin and with the prior art compound trans-[(PtCl(NH$_3$)$_2$)$_2$ H$_2$N—(CH$_2$)$_6$—NH$_2$] (NO$_3$)$_2$, described in WO 91103482.

Table I—Cytotoxic activity of cisplatin, the prior art compound trans-[(PtCl(NH$_3$)$_2$)$_2$ H$_2$N—(CH$_2$)$_6$—NH2] (NO$_3$)$_2$ and representative compounds of the invention against L1210, L1210/CDDP, A2780 and A2780/CDDP cell lines

TABLE 1

Cytotoxic activity of cisplatin, the prior art compound trans-[(PtCl(NH$_3$)$_2$)$_2$ H$_2$N—(CH$_2$)$_6$—NH2](NO$_3$)$_2$ and representative compounds of the invention against L1210, L1210/CDDP, A2780 and A2780/CDDP cell lines

| compound | example | L1210 IC$_{50}$ 2h$^a$ | L1210/CDDP IC$_{50}$ 2h$^a$ | A2780 IC$_{50}$ 1h$^b$ | A2780/CDDP IC$_{50}$ 1h$^b$ |
|---|---|---|---|---|---|
| A | 2 | 1.14 | 1.06 | 0.68 | 2.15 |
| B | 1 | 1.39 | 1.46 | 0.25 | 1.9 |
| [trans-(PtCl(NH$_3$)$_2$)$_2$ H$_2$N—(CH$_2$)$_6$—NH$_2$](NO$_3$)$_2$ | — | 3.7 | 15.6 | 2.3 | 23.8 |
| cisplatin | — | 1.33 | 59 | 2.4 | 16.1 |

$^a$IC50 (concentration of the drug expressed as (g/ml which causes a 50% inhibition of the cell growth) determined after 2 hours from the drug exposure in the non-resistant and in resistant cell line.
$^b$IC50 determined after 1 hour from the drug exposure in the non-resistant and in the resistant cell lines, respectively.
compound A = [trans-(PtCl(NH$_3$)$_2$)$_2$ H$_2$N—(CH$_2$)$_6$—NHCO—CONH—(CH$_2$)$_6$—NH$_2$](NO$_3$)$_2$
compound B = [trans-(PtCl(NH$_3$)$_2$)$_2$ H$_2$N—(CH$_2$)$_6$—NHCONH—(CH$_2$)$_6$—NH$_2$](NO$_3$)$_2$ As can be seen, the compounds of the invention are able to overcome the resistance mechanism which limits the use of cisplatin. This is undoubtedly an important feature of the compounds of the invention.

Moreover, when compared with the prior art compound trans-[(PtCl(NH$_3$)$_2$)$_2$ H$_2$N—(CH$_2$)$_6$—NH$_2$](NO$_3$)$_2$, they show to have retained a high activity, similar to or better than that of cisplatin, even in the non resistant cell lines.

In addition, the compounds of the invention were tested in an "in vivo" test in which L1210 tumor cells are inoculated intraperitoneally (ip) in a mouse and the compound is administered ip 24, 120 and 216 hours after tumor inoculation. The compounds evidenced a high antitumor effect in such an experimental model too.

The compounds of formula (I), when administered to humans and animals bearing tumors which can be treated with cisplatin or to which they are resistant, at doses ranging from 0.1 mg to 1.2 g per square metre of body area, are capable of inducing the regression of said tumors.

More generally, the compounds of the invention can be used for the treatment of the same pathological conditions for which cisplatin is used. This includes the treatment of tumors, sensitization or enhancement of radiations [Douple et al., Cisplatin Current Status and Developments, Ed. A. W. Prestayk et al., Academic Press, 125 (1980); Douple et al., Platinum Metals Res., 29, 118 (1985)] and the treatment of parasitic diseases such as African sleeping sickness [Farrell et al., Biochem. Pharmacol., 33, 961 (1984)].

Therefore, another object of the present invention is a method of treating mammals bearing tumors which can be treated with cisplatin or to which they are resistant with effective antitumor amounts of at least one compound of formula (I).

The effective dosage of the compounds of the invention can-be determined by expert clinicians according to conventional methods. The relationship between the dosages used for animals of various species and sizes and those for humans (on the basis of mg/m2 body area) is described by Freirech et al., Quantitative Comparison of Toxicity of Anticancer Agents in Mouse, Rat, Hamster, Dog, Monkey and Man, Cancer Chemother. Rep., 50, N. 4, 219–244 (1966).

Usually, however, the patient will receive doses from 0.1 to 1200 mg/kg body weight of the complex, with a dosage regimen which will vary depending on various factors which are well known to the expert clinicians.

Sometimes it can prove advantageous to administer the platinum complex of the present invention together with one or more agents which enhance the antitumor activity or relieve the undesirable side effects which may be associated with the platinum complex therapy.

For example, the platinum complexes of the present invention can be administered together with reduced glutathione, as disclosed in GB 2174905 and U.S. Pat. No. 4,871,528.

Moreover, it can be advantageous to administer the platinum complexes of the present invention in combination with other platinum complexes having antitumor activity.

A pharmaceutical composition containing at least one compound of formula (I) in combination with a platinum complex having antitumor activity is a further object of the present invention.

The treatment regimen can suitably be varied, as it is well known to the expert clinician, according to the type of tumor to be treated and the conditions of the patient.

The compounds of the invention are preferably administered as sterile aqueous solutions, optionally containing sodium chloride in suitable concentration (0.1-0-9 mg/ml). The solutions are preferably administered by the intravenous (iv) or intra-arterial (ia) routes, even though other administration forms can be used in particular cases.

The pharmaceutical compositions for the parenteral administration comprise sterile saline solutions, as defined above, or sterile powders for the extemporary preparation of the solutions, as well as oily preparations for intramuscular (im) or intraperitoneal (ip) administrations.

Other useful pharmaceutical compositions can be syrups or similar liquid forms, as well as solid forms such as tablets, capsules and the like, useful for oral administration (os).

The pharmaceutical compositions according to the present invention are prepared following known methods, such as those reported in Remington's Pharmaceutical Sciences Handbook, XVII Ed., Mack Pub., N.Y., U.S.A..

A further object of the present invention are pharmaceutical compositions containing a therapeutically effective amount of at least one compound of formula (I) in admixture with conventional carriers and excipients.

The invention is further illustrated by the following examples.

PREPARATION 1—N—BOC 6-aminohexanoic acid

6-Aminohexanoic acid (10 g) was dissolved into a water solution of potassium carbonate (7.85 g in 80 ml water) at room temperature. A solution of di-tert-butyl dicarbonate (19.4 g) in ethylene glycol dimethyl ether (65 ml) was added at room temperature and the reaction mixture was stirred overnight. Then, after cooling to 0–5° C., 6 N hydrochloric acid was dropped into the mixture in order to reach pH=2.

The muddy suspension was extracted with ethyl acetate (2×100 ml). The combined organic extracts were washed with brine (2×50 ml), dried over sodium sulfate and concentrated to a little volume. The oily residue (about 20 g) was dissolved in diiso-propyl ether (20 ml) and diluted with n-hexane (100 ml). After about 1 hour cooling and stirring, a white solid was collected by filtration and dried at room temperature over phosphoric anhydride to yield 14.9 g of the product, m.p. 42–44° C.

PREPARATION 2—N—BOC 1,6-diamino hexane

Under nitrogen atmosphere, a solution of di-tert-butyl dicarbonate (123.6 g) in anhydrous tetrahydrofuran (600 ml) was slowly added over a period of about 3 hours to a cooled (0–5° C.) and stirred solution of 1,6-diamino hexane (200 g) in THF (600 ml). After 3 hours at 10° C. and about 16 hours at room temperature, the solvent was almost completely removed under vacuum. The residual concentrated solution (about 300 ml) was dissolved in tert-butyl methyl ether (460 ml) and washed with 2 N sodium hydroxide (300 ml). The aqueous layer was further extracted with tert-butyl methyl ether (2×300 ml). The combined organic extracts were dried over sodium sulfate (50 g) and then concentrated to a little volume and distilled under reduced pressure (0.8 torr, 122–124° C.) to give N-tert-butyloxycarbonyl-1,6-diaminohexane (72 g). The distillation heads contain the excess of hexane diamine which can be recovered for another reaction.

PREPARATION 3—(N—BOC—6-aminohexyl)—N'—BOC—6-aminocapronamide

Under a nitrogen atmosphere, 1,1'-carbonyl diimidazole (1.7 g) was added portionwise in about 30 minutes to a stirred solution of N—BOC 6-aminohexanoic acid (2 g) in tetrahydrofuran (20 ml) cooled to 0–5° C. At the end of the addition the temperature was brought to 25° C. and stirring was continued for one additional hour. Then a solution of N—BOC—1,6-diamino hexane (1.87 g) in tetrahydrofuran (5 ml) was added to the reaction mixture which was stirred overnight at room temperature. After solvent removal, the residue was dissolved in chloroform (50 ml) and washed with brine, dried over sodium sulfate and concentrated under vacuum. The oily residue (4.5 g) was dissolved in diethyl ether (10 ml) and diluted with n-hexane (50 ml) in order to induce the crystallization. After 1 hour stirring at room temperature, a white solid was collected by filtration, affording, after drying, 3.5 g of the product, m.p. 83–85° C.

PREPARATION 4—N—(6-aminohexyl)6-aminocapronamide

A solution of (N—BOC—6-aminohexyl)—N'—BOC—6-aminocapronamide (5.3 g) in methylene chloride (50 ml) and trifluoroacetic acid (9.5 ml) was stirred overnight at room temperature. The reaction mixture was cautiously added to cool 6 N sodium hydroxide (100 ml), the chlorinated solvent was separated and the aqueous layer was further extracted with methylene chloride (6×50 ml). The combined organic extracts were dried over sodium sulfate and concentrated under vacuum to yield 2.34 g of the product as a colorless oil which tends to become solid upon standing.

PREPARATION 5—N—(7-aminoheptyl)-8-aminooctaneamide

According to the procedures described in preparations 1–4, starting from 7-aminoheptanoic acid the title compound is obtained.

Elem. Anal. (% calcd/found) of the hydrochloride salt: C 52.32/52.23: H 10.24/10.25; N 12.20/12.04; Cl 20.59/19.93.

PREPARATION 6

According to the procedures of preparations 1–4, the following compounds are obtained:

N-(6-aminohexanoyl)-heptanediamine;

N-(4-aminobutirroyl)-hexanediamine;

N-(5-aminopentanoyl)-octanediamine;

N-(3-aminopropanoyl)-butanediamine;

N-(7-aminoheptanoyl)-octanediamine;

N,N'-(bis-(6-aminohexanoyl))hexanediamine;

N,N'-(bis-(7-aminoheptanoyl))octanediamine;

N,N'-(bis-(2-aminoacetyl))ethanediamine;

N,N'-(bis-(2-aminoacetyl))pentanediamine;

N,N'-(bis-(4-aminobutanoyl))hexanediamine;

N,N'-(bis-(3-aminopropanoyl))butanediamine;

N,N'-(bis-(8-aminooctanoyl))octanediamine;

N,N'-(bis-(5-aminopentanoyl))heptanediamine.

PREPARATION 7—N,N'-bis[6-(tert-butyloxycarbonylamino)hexyl]urea

A solution of N-(tert-butyloxycarbonyl)-1,6-hexanediamine (g 5.11) in 51 ml of anhydrous tetraydrofuran is cooled to 0° C. and N,N'-carbonyldiimidazole (g 1.95) is added. The temperature is then raised to room temperature and the reaction mixture is kept under stirring overnight. Water (150 ml) is then added and the resulting mixture is extracted with ethyl acetate (3×40 ml). The organic extracts are collected and concentrated to a little volume, until a solid crystallizes, which after 30 minutes under stirring is filtered. 4.3 g of the product are obtained, m.p. 91–93° C.

PREPARATION 8—N,N'-bis(6-aminohexyl)urea

To a solution of N,N'-bis(6-(N-BOC)aminohexyl)urea (4.7 g; preparation 7) in 61 ml of methylene chloride, at room temperature and under stirring, 7.82 ml of trifluoroacetic acid are added and the reaction mixture is kept under stirring overnight. The solvent is evaporated off under reduced pressure and the residue is added with 10% sodium hydroxide solution saturated with sodium chloride (150 ml), then it is extracted with methylene chloride (3×40 ml). The organic extracts are collected, dried over sodium sulfate and concentrated to a little volume (about 10 ml). By adding 30 ml of tert-butyl methyl ether the product crystallizes (2 g), m.p. 90–91° C.

PREPARATION 9

According to the procedures described in preparations 7 and 8, the following intermediates are obtained:

N,N'-bis(8-aminooctyl)urea;

N,N'-bis(2-aminoethyl)urea;

N,N'-bis(5-aminopentyl)urea;

N-(6-aminohexyl)-N'-(4-aminobutyl)urea;

N-(7-aminoheptyl)-N'-(8-aminooctyl)urea;

N-(3-aminopropyl)-N'-(5-aminopentyl)urea;

N-(2-aminoethyl)-N'-(4-aminobutyl)urea.

PREPARATION 10—N,N'-bis[6-(tert-butyloxycarbonylamino)hexyl]oxalamide

A solution of N—BOC hexanediamine (10 g) and triethylamine (9.65 ml) in 90 ml of anhydrous methylene chloride is cooled to 0° C. and a solution of oxalyl chloride (2.015 ml) in 6 ml of methylene chloride is added dropwise in 30 minutes. The reaction is exotermic. The temperature is then raised to room temperature and the reaction mixture is kept under stirring for 4 hours. The reaction is worked out by pouring it into ice/water. After 30 minutes a solid precipitates, which is recovered and treated with 40 ml of ethyl acetate under stirring for 30 minutes. 4.2 g of the product are obtained, m.p. 174–178° C.

PREPARATION 11—N,N'-bis(6-aminohexyl)oxalamide

A solution of N,N'-bis[6-(tert-butyloxycarbonylamino) hexyl]oxalamide (4 g) and trifluoroacetic acid (6.3 ml) in 50 ml of methylene chloride is kept under stirring for 24 hours. The above colorless methylene chloride phase is separated by decantation and the reaction phase is added dropwise to a 20% sodium hydroxide solution (150 ml) kept at 10° C. An amorphous solid precipitates, which is extracted with methylene chloride (3×150 ml). The collected organic extracts are dried over sodium sulfate, then they are concentrated to about 10 ml. By adding 150 ml of tert-butyl methyl ether a soild precipitates, which is kept under stirring for additional 2 hours 20 minutes. 1.4 g of the product are obtained, m.p. 115–116° C.

PREPARATION 12

According to the procedures described in preparations 10 and 11, the following intermediates are obtained:

N,N'-bis(8-aminooctyl)oxalamide;

N,N'-bis(2-aminoethyl) oxalamide;

N,N'-bis(5-aminopentyl) oxalamide;

N-(6-aminohexyl)-N'-(4-aminobutyl) oxalamide;

N-(7-aminoheptyl)-N'-(8-aminooctyl) oxalamide;

N-(3-aminopropyl)-N'-(5-aminopentyl) oxalamide;

N-(2-aminoethyl)-N'-(4-aminobutyl) oxalamide.

EXAMPLE 1

$[(trans\text{-}PtCl(NH_3)_2)_2\ H_2N\text{—}(CH_2)_6\text{—}NHCONH\text{—}(CH_2)_6\text{—}NH_2](NO_3)_2$ To a solution of 1 g of trans-platin in 100 ml of dimethylformamide were added 0.53 g of silver nitrate. The mixture was stirred at room temperature under exclusion of light for 18 hours. After filtration of the silver chloride precipitate, 0.35 g of N,N'-bis(6-aminohexyl)urea in 25 ml of dimethylformamide were added dropwise to the filtrate at −20° C. within 0.5 hours. After being stirred 1 hour at −20° C. and further 2 hours at room temperature, 1 g of active carbon was added to the mixture, which was stirred for 0.5 hours. The solution was filtered and evaporated to 50–60 ml and 50 ml of diethyl ether were poured into the solution to precipitate the white product which was filtered off and stirred for 2 days in 25 ml of acetone. The compound was filtered off and stirred for 18 hours in 20 ml of methanol. Finally the white complex was collected by vacuum filtration, washed with diethyl ether and dried at 56° C. in vacuo.

$^1$H NMR in $D_2O$: 3.08, 2.68, 1.67, 1.47, 1.35 ppm.

Elem. analysis (% calcd/found): C 17.13/17.38; H 4.64/4.68; N 15.37/15.20; Cl 7.78/7.64; Pt 42.80/42.19.

EXAMPLE 2

According to the method described in example 1, starting from the appropriate polymethylene derivative from preparations 9 or 12, the following complexes are obtained:

$[(trans\text{-}PtCl(NH_3)_2)_2\ H_2N\text{—}(CH_2)_8\text{—}NHCONH\text{—}(CH_2)_8\text{—}NH_2](NO_3)_2$;

$[(trans\text{-}PtCl(NH_3)_2)_2\ H_2N\text{—}(CH_2)_2\text{—}NHCONH\text{—}(CH_2)_2\text{—}NH_2](NO_3)_2$;

$[(trans\text{-}PtCl(NH_3)_2)_2\ H_2N\text{—}(CH_2)_5\text{—}NHCONH\text{—}(CH_2)_5\text{—}NH_2](NO_3)_2$;

$[(trans\text{-}PtCl(NH_3)_2)_2\ H_2N\text{—}(CH_2)_6\text{—}NHCONH\text{—}(CH_2)_4\text{—}NH_2](NO_3)_2$;

$[(trans\text{-}PtCl(NH_3)_2)_2\ H_2N\text{—}(CH_2)_7\text{—}NHCONH\text{—}(CH_2)_8\text{—}NH_2](NO_3)_2$;

$[(trans\text{-}PtCl(NH_3)_2)_2\ H_2N\text{—}(CH_2)_3\text{—}NHCONH\text{—}(CH_2)_5\text{—}NH_2](NO_3)_2$;

$[(trans\text{-}PtCl(NH_3)_2)_2\ H_2N\text{—}(CH_2)_2\text{—}NHCONH\text{—}(CH_2)_4\text{—}NH_2](NO_3)_2$;

$[(trans\text{-}PtCl(NH_3)_2)_2\ H_2N\text{—}(CH_2)_6\text{—}NHCO\text{—}CONH\text{—}(CH_2)_6\text{—}NH_2](NO_3)_2$, $^1$H NMR in D20: 3.12, 2.65, 1.63,1.49,1.37ppm, Elem. analysis (% calcd/found): C 17.90/18.13; H 4.51/4.48; N 14.91/14.93; Cl 7.55/7.55;

$[(trans\text{-}PtCl(NH_3)_2)_2\ H_2N\text{—}(CH_2)_8\text{—}NHCO\text{—}CONH\text{—}(CH_2)_8\text{—}NH_2](NO_3)_2$;

$[(trans\text{-}PtCl(NH_3)_2)_2\ H_2N\text{—}(CH_2)_2\text{—}NHCO\text{—}CONH\text{—}(CH_2)_2\text{—}NH_2](NO_3)_2$;

$[(trans\text{-}PtCl(NH_3)_2)_2\ H_2N\text{—}(CH_2)_5\text{—}NHCO\text{—}CONH\text{—}(CH_2)_5\text{—}NH_2](NO_3)_2$;

$[(trans\text{-}PtCl(NH_3)_2)_2\ H_2N\text{—}(CH_2)_6\text{—}NHCO\text{—}CONH\text{—}(CH_2)_4\text{—}NH_2](NO_3)_2$;

$[(trans\text{-}PtCl(NH_3)_2)_2\ H_2N\text{—}(CH_2)_7\text{—}NHCO\text{—}CONH\text{—}(CH_2)_8\text{—}NH_2](NO_3)_2$;

$[(trans\text{-}PtCl(NH_3)_2)_2\ H_2N\text{—}(CH_2)_3\text{—}NHCO\text{—}CONH\text{—}(CH_2)_5\text{—}NH_2](NO_3)_2$;

$[(trans\text{-}PtCl(NH_3)_2)_2\ H_2N\text{—}(CH_2)_2\text{—}NHCO\text{—}CONH\text{—}(CH_2)_4\text{—}NH_2](NO_3)_2$.

EXAMPLE 3

$[(trans\text{-}PtCl(NH_3)_2)_2\ H_2N\text{—}(CH_2)_7\text{—}CONH\text{—}(CH_2)_7\text{—}NH_2](NO_3)_2$ To a solution of trans-platin (g 1.94) in 215 ml of anhydrous dimethylformamide are added, under stirring and at room temperature, 1.09 g of silver nitrate and the reaction mixture is stirred under exclusion of light for 18 hours, then the precipitated silver chloride is filtered off. The resulting yellow clear solution is cooled to −20/−15° C. and a solution of the compound of preparation 5 (0.701 g) in 32 ml of dimethylformamide is added dropwise in about 30 minutes. After 3 hours at −20° C. and additional 3 hours at room temperature 2 g of charcoal are added and the suspension is stirred for 15 minutes, then it is filtered and the clear solution is diluted with acetone until a precipitation occurs (about 1.01 l). The precipitate is kept under stirring overnight, then it is recovered by filtration, obtaining 1.13 g of the product. By diluting the mother liquors with acetone (760 ml) additional 419 mg of the product are obtained.

The product can be recrystallized by dissolving it in methanol/dimethylformamide 2:1 and reprecipitating it by adding acetone (about 10:1 with respect to dimethylformamide).

$^1$H N.M.R. in D20: 1.35 ppm (m, 12 H); 1.62 ppm (m, 8 H); 2.25 ppm (t, 2 H); 2.70 ppm (m, 4 H); 3.20 ppm (t, 2 H).

EXAMPLE 4

According to the procedure described in example 3, starting from the appropriate polymethylene intermediates of preparation 6, the following platinum complexes are prepared:

[(trans-PtCl(NH₃)₂)₂ H₂N—(CH₂)₅—CONH—(CH₂)₇—NH₂](NO₃)₂;

[(trans-PtCl(NH₃)₂)₂ H₂N—(CH₂)₃—CONH—(CH₂)₆—NH₂](NO₃)₂;

[(trans-PtCl(NH₃)₂)₂ H₂N—(CH₂)₄—CONH—(CH₂)₈—NH₂](NO₃)₂;

[(trans-PtCl(NH₃)₂)₂ H₂N—(CH₂)₂—CONH—(CH₂)₄—NH₂](NO₃)₂;

[(trans-PtCl(NH₃)₂)₂ H₂N—(CH₂)₆—CONH—(CH₂)₈—NH₂](NO₃)₂;

[(trans-PtCl(NH₃)₂)₂ H₂N—(CH₂)₅—CONH—(CH₂)₆—NHCO—(CH₂)₅—NH₂](NO₃)₂;

[(trans-PtCl(NH₃)₂)₂ H₂N—(CH₂)₆—CONH—(CH₂)₈—NHCO—(CH₂)₆—NH₂](NO₃)₂;

[(trans-PtCl(NH₃)₂)₂ H₂N—CH₂—CONH—(CH₂)₂—NHCO—CH₂—NH₂](NO₃)₂;

[(trans-PtCl(NH₃)₂)₂ H₂N—CH₂—CONH—(CH₂)₅—NHCO—CH₂—NH₂](NO₃)₂;

[(trans-PtCl(NH₃)₂)₂ H₂N—(CH₂)₃—CONH—(CH₂)₆—NHCO—(CH₂)₅—NH₂](NO₃)₂;

[(trans-PtCl(NH₃)₂)₂ H₂N—(CH₂)₇—CONH—(CH₂)₈—NHCO—(CH₂)₇—NH₂](NO₃)₂;

[(trans-PtCl(NH₃)₂)₂ H₂N—(CH₂)₄—CONH—(CH₂)₇—NHCO—(CH₂)₄—NH₂](NO₃)₂.

[trans-(PtCl(NH₃)₂)₂(H₂N—(CH₂)₇—CONH—(CH₂)₇—NH₂)]dinitrate,

¹H-NMR in D₂O: 3.2 ppm (t, 2 H); 2.55–2.85 ppm (m, 4 H); 2.25 ppm (t, 2 H); 1.45–1.8 ppm (m, 8 H); 1.35 ppm (br s, 12 H), ¹⁹⁵Pt-NMR in NaCl/D₂O: −2421 ppm, Elem. Anal. % calcd/found: C 19.48/19.24; H 4.90/4.89; N 13.63/13.48; Cl 7.67/7.56; Pt 42.20/41.29;

[trans-(PtCl(NH₃)₂)₂(H₂N—(CH₂)₅—CONH—(CH₂)₆—NH₂)]dinitrate,

¹H-NMR in D₂O: 3.2 ppm (t, 2 H); 2.7 ppm (br q, 4 H); 2.2 ppm (t, 2 H); 1.2–1.8 ppm (m, 14 H), Elem. Anal. % calcd/found: C 16.33/16.21; H 4.45/4.35; N 14.28/14.19; Cl 8.03/7.95; Pt 44.21/43.42;

[trans-(PtCl(NH₃)₂)₂(H₂N—(CH₂)₅—CONH—(CH₂)₂—NHCO—(CH₂)₅—NH₂)]dinitrate,

¹H-NMR in D₂O: 3.3 ppm (s, 4 H); 2.7 ppm (m, 4 H); 2.2 ppm (t, 4 H); 1.3–1.7 ppm (m, 12 H), Elem. Anal. % calcd/found: C 17.92/17.92; H 4.51/4.18; N 14.91/14.35; Cl 7.55/7.06; Pt 41.52/41.92.

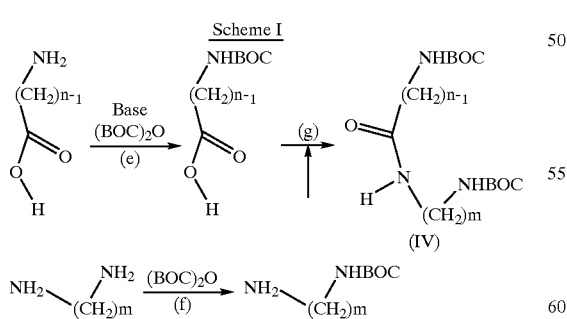

Scheme I

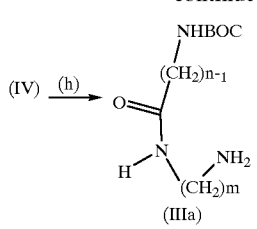

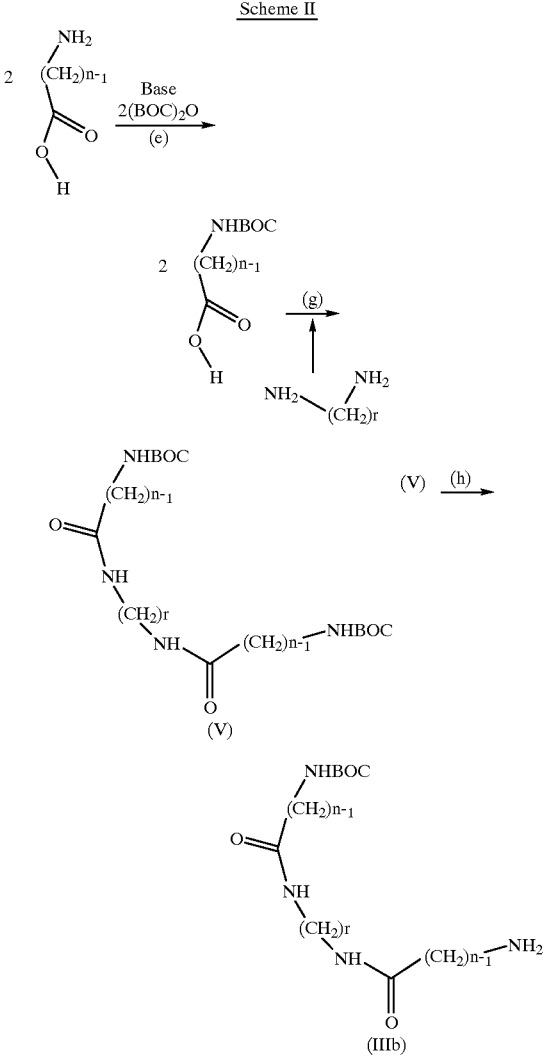

Scheme II

Scheme III
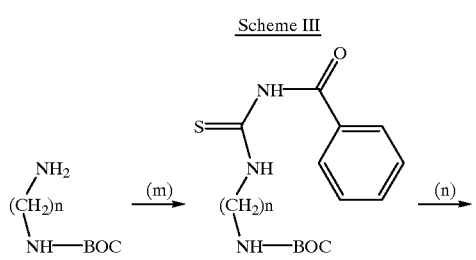
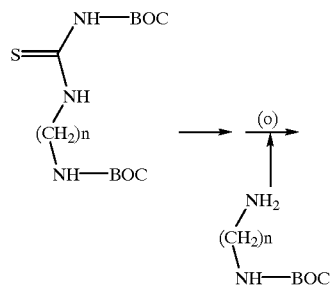
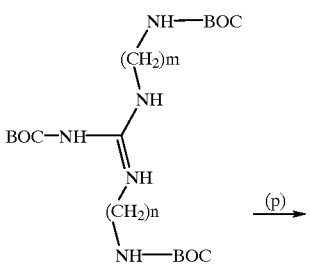
(IIId) R² = H
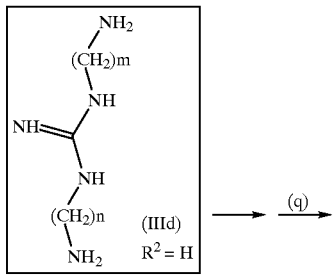
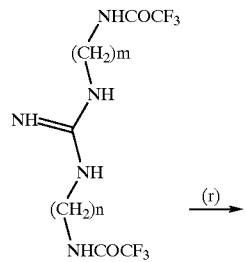
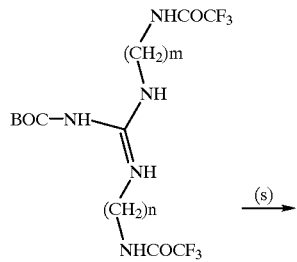
(IIId) R² = BOC
Scheme IV
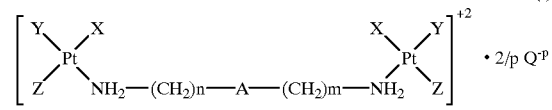
What is claimed is:
1. A bis-platinum(II) complex comprising formula (I):
$$\left[ \begin{array}{c} Y \\ Z \end{array} \begin{array}{c} X \\ Pt \\ NH_2-(CH_2)n-A-(CH_2)m-NH_2 \end{array} \begin{array}{c} X \\ Pt \\ Z \end{array} \begin{array}{c} Y \\ \end{array} \right]^{+2} \cdot 2/p\ Q^{-p} \quad (I)$$
wherein two of the X, Y, and Z ligands attached to each platinum atom are ammonia and the other ligand is selected from the group consisting of chloride, bromide, iodide, and a ($C_1$–$C_4$)acyloxy group;

n and m are each independently an integer of two to eight;

p is the integer one or two;

A is —$B_1$— or —$B_2$—$(CH_2)_r$—$B_2$—, wherein r is an integer of two to eight, $B_1$ is selected from the group consisting of —$NR^1$—CO—, —CO—$NR^1$—, —$NR^1$—$SO_2$—$NR^1$—, —$NR^1$—C(=$NR^2$)—$NR^1$—, —$NR^1$—CO—CO—$NR^1$—, and —$NR^1$—CO—$NR^1$—, and $B_2$ is —$NR^1$—CO— or —CO—$NR^1$—, wherein $R^1$ is hydrogen or a ($C_1$–$C_4$)alkyl group, and wherein $R^2$ is selected from the group consisting of hydrogen, ($C_1$–$C_4$)alkyl, and tert-butyloxycarbonyl; and $Q^{-p}$ is an anion selected from the group consisting of chloride, bromide, iodide, nitrate, sulfate, hydrogen sulfate and perchlorate.

2. The complex of claim 1, wherein $B_1$ is selected from the group consisting of —NHCO—, —CONH—, —NHCONH—, and —NHCO—CONH—.

3. The complex of claim 1, wherein the ligands X and Z are ammonia and are attached to each platinum atom in the trans position.

4. A method of preparing a bis-platinum(II) complex of claim 1, comprising the steps of reacting a precursor of formula [Pt(X)(Y)(Z)Cl] with dimethylformamide in the presence of an equimolar amount of $AgNO_3$, at a temperature of about 0° C. to about 50° C., to produce the activated intermediate of formula (II):

[Pt(X)(Y)(Z)(DMF)]$^{+\circ}$ $NO_3^-$  (II);

condensing two moles of intermediate (II) with a polymethylene derivative of formula (III):

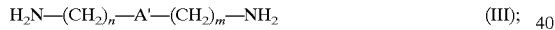

$H_2N$—$(CH_2)_n$—A'—$(CH_2)_m$—$NH_2$  (III);

at a temperature of about −40° C. to about room temperature, wherein n and m are each independently an integer of two to eight, and A' has the meaning of A, as defined above, or A' is a group that can be converted into A by the removal of suitable protecting groups, to produce a platinum complex of formula (I'):

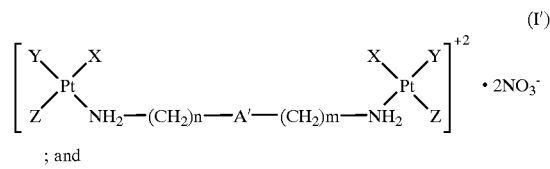

; and separating by chromatography any diastereomers formed.

5. The method claim 4, wherein A' has a protecting group generally used for molecules containing nitrogen atoms, and A' is a group which can be converted into A by removing the protecting group from the complex of formula (I') following the condensing step.

6. The method of claim 5, wherein the protecting group is a tert-butyloxycarbonyl group.

7. The method of claim 4, wherein the reaction of the precursor is performed at about room temperature.

8. The method of claim 4, wherein the condensing is performed at a temperature of about −20° C.

9. A method of treating leukemia, ovarian carcinoma, lung tumors or cisplatin-resistant or cisplatin-treatable tumors in a mammal comprising the step of administering to the mammal a leukemia, ovarian carcinoma, lung tumor or cisplatin-resistant or cisplatin-treatable tumor treating effective amount of at least one bis-platinum(II) complex of claim 1.

10. The method of claim 9, wherein a bis-platinum(II) complex is administered with at least one agent which enhances the antitumor activity of the complex.

11. The method of claim 9, wherein the complex is administered as a sterile aqueous solution.

12. The method of claim 11, wherein aqueous solution further comprises sodium chloride in a concentration between 0.1 and 0.9 mg/ml.

13. The method of claim 9, wherein the at least one complex is administered orally.

14. The method of claim 9, wherein the tumor treating effecitve amount is a dose of about 0.1 mg to about 1.2 g of complex per square metre of body area of the mammal.

15. A pharmaceutical composition, comprising a bis-platinum(II) complex according to claim 1 in combination with a pharmaceutically acceptable carrier or excipient.

* * * * *